United States Patent [19]

Hsu

[11] 4,424,380

[45] Jan. 3, 1984

[54] HYDROFORMYLATION CATALYST AND PROCESS OF USING IT

[75] Inventor: Chao-Yang Hsu, Media, Pa.

[73] Assignee: Sun Tech, Inc., Philadelphia, Pa.

[21] Appl. No.: 327,867

[22] Filed: Dec. 7, 1981

[51] Int. Cl.$^3$ .............................................. C07C 45/50
[52] U.S. Cl. .................... 568/454; 568/909; 502/162; 502/169
[58] Field of Search .............................. 568/454, 909; 252/431 R

[56] References Cited

U.S. PATENT DOCUMENTS

| | | | |
|---|---|---|---|
| 3,876,672 | 4/1975 | Mrewca | 568/454 |
| 3,981,925 | 9/1976 | Schwager et al. | 568/454 |
| 3,996,293 | 12/1976 | Knifton et al. | 568/454 |
| 4,013,583 | 3/1977 | Knifton | 568/454 |
| 4,013,584 | 3/1977 | Knifton | 568/454 |
| 4,101,565 | 7/1978 | Poist | 568/454 |
| 4,155,939 | 5/1979 | Poist | 568/454 |
| 4,198,352 | 4/1980 | Kim et al. | 568/454 |
| 4,283,563 | 8/1981 | Kawabata et al. | 568/454 |
| 4,299,985 | 11/1981 | Knifton et al. | 568/454 |

OTHER PUBLICATIONS

Hsu et al., "J. Amer. Chem. Soc." vol. 97, p. 353 (1975).
Schwager et al., "J. Cat." vol. 45, p. 226 (1976).
Kawabata et al., "J. Chem. Soc. Chem. Comm." p. 462 (1979).

*Primary Examiner*—Werren B. Lone
*Attorney, Agent, or Firm*—J. Edward Hess; Donald R. Johnson; Patrick C. Baker

[57] ABSTRACT

A novel catalyst and the process of using it for hydroformylation where the catalyst is a complex of the formula Pt(Acetylacetonate)$_2$/nMX$_2$.nH$_2$O/xPR$_3$ where M is a Group IVA metal, X is a halogem atom, n is an integer of from about 2 to about 10, x is an integer of from about 5 to about 20, n is 0 or 2, and PR$_3$ is a phosphine where R is an alkyl or, aryl group.

9 Claims, No Drawings

HYDROFORMYLATION CATALYST AND PROCESS OF USING IT

BACKGROUND OF THE INVENTION

The use of platinum II complexes as a catalyst for hydroformylation (OXO reaction) is known. Thus, for example, $PtH(SnCl_3)(PPh_3)_2$ are shown by Hsu and Orchin, J. Amer. Chem Soc., 97 353 (1975) to be useful for conversion of 1-pentene to aldehydes. Schwager and Knifton, J. Cat. 45, 256 (1976), U.S. Pat. No. 3,981,925 and U.S. Pat. No. 3,996,293 disclose use of $PtCl_2(PPh_3)_2 + SnCl_2$ for a similar reaction with 1-heptene. Kawabata, et al., J.C.S. Chem. Comm 462 (1979) teach $Pt(PhCN)_2Cl_2 + Ph_2P(CH_2)_xPPh_2$ for conversion of 1-pentene to aldehydes. U.S. Pat. Nos. 4,101,565 and 4,155,939 show the dimer $(PtCl_2PPh_3)_2 + SnCl_2$ for hydroformylation of 1-hexene. U.S. Pat. No. 3,876,672 also shows hydroformylation of 1-hexene with $PtH(PPh_3)_3{}^+HSO_4{}^-$.

In the hydroformylation reaction of olefin with such catalysts the reaction proceeds as follows:

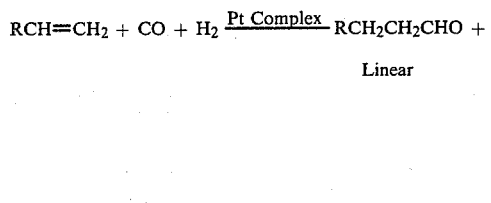

In such reactions, usually greater than 90% selectivity (relative to total aldehydes) to linear aldehydes is obtained when a platinum complex is employed as a catalyst. However, when propylene is the olefin, lower yield and selectivity to linear aldehyde (n-butyraldehyde) is obtained and this is shown by the work of Knifton and his associates referred to above. It is to be understood that with a chemical commodity such as n-butyraldehyde, even a small increase in selectivity to the desired linear product is highly desirable because of the large volumes processed. This invention provides a novel catalyst which gives improved selectivity and yield to linear aldehydes particularly for n-butyraldehyde and thus makes a significant advance in the art.

STATEMENT OF INVENTION

This invention provides a novel hydroformylation catalyst which is a complex characterized by the formula $Pt(Acetylacetonate)_2/MX_2nH_2O/PR_3$ where M is a Group IVA metal, X is halogen atom n is 0 or 2, and $PR_3$ is a phosphine where R is an alkyl, aryl or mixed alkyl-aryl group. The invention also embodies the hydroformylation process with the novel catalyst.

DISCUSSION OF INVENTION

The hydroformylation reaction is also known as the OXO process and is well known in the art (see for example Kirk-Othmer Encyclopedia of Chemical Technology). The catalyst of the invention may be employed under the usual conditions for such reactions, but preferred reaction conditions will be from about 20° to about 150° C. (preferably from about 75° to about 110°) at elevated pressure of from about 250 to about 3000 psig. The amount of catalyst may vary over a wide range; e.g., from about 0.01 to about at 5% of olefins used (preferably from about 0.1 to about 1% with about 0.4% being most preferred).

The novel catalyst is employed in a homogeneous system and the solvents used will be selected from a wide variety of known solvents for the OXO reaction such as aromatic hydrocarbons, aldehydes, ketones, acetophenone, and the like. The catalyst is easily made simply by mixing together in the solvent the catalyst components of platinum acetylacetonate $(PtAcAc)_2$, a metal salt of formula $MX_2$ where M is a Group IVA metal such as tin (preferred), germanium or lead, and X is a halogen atom (chlorine preferred), which salt may be anhydrous (n=0) or the dihydrate (n=2), and a phosphine of formula $PR_3$ where R is an alkyl or aryl group and in which the three R groups of the phosphine may be the same or different. The R groups of the phosphine will generally contain from one to six carbon atoms when alkyl or from six to twelve carbon atoms when aryl. Typical R groups are methyl, ethyl, hexyl, phenyl (preferred), naphthyl, tolyl, xylyl, and the like. The ratio of platinum to Group IVA metal to phosphine will vary over a wide range, but will generally be from about 2 to about 10 moles (about 5 preferred) of Group IVA metal per mole of platinum and from about 5 to about 20 (about 2.5 to about 5.0 preferred) of phosphine per mole of platinum. Thus, the catalyst may be formulated as $Pt(AcAc)_2/mMX_2nH_2O/xPR_3$ where n is from about 2 to about 10 and x is from about 5 to about 20, n, and R being identified above.

The process of the invention is operable with the wide variety of olefins susceptible to hydroformylation and will include, preferably, the $C_2$ to $C_{20}$ aliphatic and cycloaliphatic olefins.

In order to illustrate the advantages of the novel catalyst, the following examples are given.

EXAMPLE 1 (Prior Art)

This example illustrates the hydroformylation of propylene to butyraldehyde in the presence of a prior art platinum catalyst in a manner similar to that disclosed in U.S. Pat. No. 3,981,925.

To a 300 ml stainless steel autoclave was added 100 ml of toluene as solvent, 0.53 g (1.0 mmole) of $PtCl_2(PPh_3)_2$, 1.14 g (5.0 mmole) of $SnCl_2.2H_2O$, and 1.31 g (5.0 mmole) of $PPh_3$. After the mixture was stirred for 15 minutes under a nitrogen atmosphere, the autoclave was purged with syngas ($H_2/CO=1:1$) and 10.5 g (250 mmole) of propylene was added. The autoclave was then charged with syngas ($H_2/CO=1:1$) to make a total pressure of 750 psig. After which the reactor was then quickly heated to 100° C. and the syngas pressure was maintained at 1000 psig through constant addition of syngas from a reservoir. After 4 hours of reaction, the autoclave was cooled to room temperature and the gas phase materials were vented. The liquid contents were removed and analyzed directly by vapor phase chromatography. Analysis of the reaction mixture indicated that 85% yield of butyraldehydes was obtained and the molar ratio of n-butyraldehyde to iso-butyraldehyde was 6.7 (i.e., 87% of normal aldehyde).

EXAMPLE 2 (The Invention)

This example illustrates the hydroformylation of propylene to butyraldehyde in the presence of a catalyst of the present invention.

In a manner similar to that described in Example 1, an autoclave was charged with 100 ml of toluene, 0.39 g (1.0 mmole) of Pt(AcAc)$_2$, 1.14 g (5.0 mmole) of SnCl$_2$.2H$_2$O, and 1.31 g (5.0 mmole) of PPh$_3$. After the mixture was stirred for 15 minutes under nitrogen atmosphere, the autoclave was purged with syngas (H$_2$/CO=1:1) and 10.5 g (250 mmole) of propylene was added. The autoclave was then charged with 750 psig of syngas (H$_2$/CO=1:1) and quickly heated to 100° C., whereupon the total pressure was adjusted to 1000 psig by the use of a syngas reservoir. After 5 hours of reaction, the autoclave was cooled, and the liquid mixture was analyzed using vapor phase chromatography. Analytical data indicated the yield of butyraldehyde was 95% and the ratio of n-butyraldehyde to iso-butyraldehyde was 21 to 1, corresponding to 96% of normal butyraldehyde.

EXAMPLES 3-5

In these examples, summarized in Table I, the reaction procedure is similar to that shown in Example 2. The main difference is in the variation of reaction temperature as illustrated in these examples. Higher normal to iso-butyraldehyde ratio was obtained when the reaction temperature was lowered.

EXAMPLES 6-11

In these examples, summarized in Table II, the reaction procedures are similar to that shown in Example 2, the major differences are the variation in syngas total pressure and the ratio of H$_2$ to CO in syngas composition.

EXAMPLES 12-17

In these examples, summarized in Table III, the reaction procedures are similar to that shown in Example 2, the major differences are the use of various types of solvents.

EXAMPLES 18-22

Variation in catalyst composition are illustrated in these examples. The reaction procedures used for these examples are similar to that described in Example 2. The reaction conditions and results are summarized in Table IV.

TABLE I

|  | Example 3 | Example 4 | Example 5 |
|---|---|---|---|
| Reagents |  |  |  |
| Propylene | 245 mmole | 238 mmole | 240 mmole |
| Pt(AcAc)$_2$ | 1.0 mmole | 1.0 mmole | 1.0 mmole |
| SnCl$_2$.2H$_2$O | 5.0 mmole | 5.0 mmole | 5.0 mmole |
| PPh$_3$ | 5.0 mmole | 5.0 mmole | 5.0 mmole |
| Toluene | 100 ml | 100 ml | 100 ml |
| H$_2$/CO (1:1) | 1000 psig | 1000 psig | 1000 psig |
| Conditions |  |  |  |
| Temperature | 80° C. | 90° C. | 100° C. |
| Reaction Time | 6 hr. | 6 hr. | 6 hr. |
| Results |  |  |  |
| Yield of C$_4$- Aldehydes | 83% | 91% | 95% |
| Ratio of n/iso-butyraldehyde | 98/2 | 97/3 | 95/5 |

TABLE II

|  | Example 6 | Example 7 | Example 8 | Example 9 | Example 10 | Example 11 |
|---|---|---|---|---|---|---|
| Reagents |  |  |  |  |  |  |
| Propylene | 254 mmole | 258 mmole | 251 mmole | 245 mmole | 250 mmole | 253 mmole |
| Pt(Acac)$_2$ | 1.0 mmole | 1.0 mmole | 1.0 mmole | 1.0 mmole | 1.0 mmole | 1.0 mmole |
| SnCl$_2$.2H$_2$O | 5.0 mmole | 5.0 mmole | 5.0 mmole | 5.0 mmole | 5.0 mmole | 5.0 mmole |
| PPh$_3$ | 5.0 mmole | 5.0 mmole | 5.0 mmole | 5.0 mmole | 5.0 mmole | 5.0 mmole |
| Solvent | Ethylbenzene (100 ml) | Ethylbenzene (100 ml) | Ethylbenzene (100 ml) | Toluene (100 ml) | Toluene (100 ml) | Toluene (100 ml) |
| H$_2$/CO (1:1) | 1000 psig | — | — | 700 psig | 1500 psig | 1250 psig |
| (2:1) | — | 1000 psig | — | — | — | — |
| (3:1) | — | — | 1000 psig | — | — | — |
| Conditions |  |  |  |  |  |  |
| Temperature | 95° C. | 95° C. | 95° C. | 100° C. | 100° C. | 100° C. |
| Reaction Time | 4.0 hr* | 5.0 hr | 5.0 hr | 5.0 hr | 5.0 hr | 5.0 hr |
| Results |  |  |  |  |  |  |
| Yield of C$_4$ - Aldehydes | 78% | 94% | 83% | 85% | 94% | 97% |
| Ratio of n/iso-butyraldehyde | 96/4 | 97/3 | 95/5 | 95/5 | 97/3 | 95/5 |

*Reaction incomplete in this time

TABLE III

|  | Example 12 | Example 13 | Example 14 | Example 15 | Example 16 | Example 17 |
|---|---|---|---|---|---|---|
| Reagents |  |  |  |  |  |  |
| Propylene | 250 mmole | 251 mmole | 246 mmole | 249 mmole | 251 mmole | 254 mmole |
| Solvent (100 ml) | Acetophenone | Acetophenone | Acetophenone | Xylenes | Tetralin | MIBK |
| Pt(AcAc) | 1.0 mmole | 1.0 mmole | 1.0 mmole | 1.0 mmole | 1.0 mmole | 1.0 mmole |
| SnCl$_2$.2H$_2$O | 5.0 mmole | 5.0 mmole | 5.0 mmole | 5.0 mmole | 5.0 mmole | 5.0 mmole |
| PPh$_3$ | 5.0 mmole | 5.0 mmole | 5.0 mmole | 5.0 mmole | 5.0 mmole | 5.0 mmole |
| H$_2$/CO (1:1) | 1000 psig | 1000 psig | 1500 psig | 1000 psig | 1000 psig | 1000 psig |
| Conditions |  |  |  |  |  |  |
| Temperature | 90° C. | 100° C. | 100° C. | 100° C. | 100° C. | 100° C. |
| Reaction Time | 5.5 hr | 6.0 hr | 5.0 hr | 4.0 hr | 4.0 hr | 4.0 hr |
| Results |  |  |  |  |  |  |
| Yield of C$_4$ - Aldehydes | 62% | 67% | 86% | 94% | 77% | 60% |
| Ratio of n/iso-butyraldehyde | 97/3 | 95/5 | 96/4 | 97/3 | 96/4 | 96/4 |

MIBK = Methyl Isobutyl Ketone

TABLE IV

|  | Example 18 | Example 19 | Example 20 | Example 21 | Example 22 |
|---|---|---|---|---|---|
| Reagents | | | | | |
| Propylene | 250 mmole | 256 mmole | 248 mmole | 250 mmole | 250 mmole |
| Pt(AcAc)$_2$ | 1.0 mmole | 1.0 mmole | 0.5 mmole | 1.0 mmole | 1.0 mmole |
| SnCl$_2$.2H$_2$O | 2.5 mmole | 2.5 mmole | 2.5 mmole | None | 5.0 mmole |
| PPh$_3$ | 5.0 mmole | 2.5 mmole | 2.5 mmole | 5.0 mmole | None |
| Ethylbenzene Solvent | 100 ml | 100 ml | 100 ml | 100 ml | 100 ml |
| H$_2$/CO (1:1) | 1000 psig | 1000 psig | 1000 psig | 1000 psig | 1000 psig |
| Conditions | | | | | |
| Temperature | 100° C. | 95° C. | 95° C. | 100° C. | 100° C. |
| Time | 4 hr | 4 hr | 5 hr | 4 hr | 4 hr |
| Results | | | | | |
| Yield of C$_4$ - Aldehydes | 93% | 80% | 60% | No Reaction | 5% |
| Ratio of n/iso-butyraldehyde | 97% | 95/5 | 96/4 | No Reaction | 50/50 |

EXAMPLE 23

This example illustrates that in the presence of the catalyst of the invention the higher olefins such as 1-pentene can be hydroformylated to give high yield of hexanal and give a high ratio of linear to branched aldehydes.

To a 300 ml stainless steel autoclave was added 100 ml of ethylbenzene solvent, 0.39 g (1.0 mmole) of Pt(AcAc)$_2$, 1.14 g (5.0 mmole) of SnCl$_2$.2H$_2$O, and 1.31 g (5.0 mmole) of PPh$_3$. After the mixture was purged with syngas (H$_2$/CO=1:1) and 17.5 g of 1-pentene (250 mmole) was added. The autoclave was then charged with 750 psig of syngas (H$_2$/CO=1:1) and quickly heated to 100° C., whereupon the total pressure was adjusted to 1000 psig by the use of a syngas reservoir. After 5 hours of reaction, the autoclave was cooled to room temperature and the excess gas was vented. The liquid reaction was removed and analyzed using vapor phase chromatography. Analytical data indicated that 95% yield of C$_6$-aldehydes was obtained. The ratio of 1-hexanal to 2-hexanal was 97 to 3.

I claim:

1. In the process of hydroformylating an olefin containing 2 to about 20 carbon atoms by reacting the olefin with hydrogen and carbon monoxide at elevated pressure in the presence of a catalyst to produce an aldehyde, the improvement of using as catalyst a complex of the formula Pt(Acetylacetonate)$_2$/mMX$_2$.nH$_2$O/xPR$_3$ where M is a Group IVA metal, X is a halogen atom, m is an integer from about 2 to about 10, n is 0 or 2, x is an integer from about 5 to about 20, and PR$_3$ is a phosphine where R is an alkyl or aryl group.

2. The process of claim 1 wherein M is tin.

3. The process of claim 1 wherein MX$_2$ is SnCl$_2$.

4. The process of claim 1 wherein the phosphine is triphenylphosphine.

5. The process of claim 1 wherein the catalyst is Pt(Acetylacetonate)$_2$/5SnCl$_2$.2H$_2$O/5PPh$_3$.

6. The process of claim 1 wherein the olefin is propylene.

7. The process of claim 5 wherein the olefin is propylene.

8. The process of claim 1 wherein the olefin is 1-pentene.

9. The process of claim 1 wherein MX$_2$ is SnCl$_2$ and the phosphine is triphenylphosphine.

* * * * *